United States Patent [19]

Wilen et al.

[11] Patent Number: 4,984,451
[45] Date of Patent: Jan. 15, 1991

[54] METHOD FOR DETERMINING PHYSICAL PROPERTIES OF LIQUIDS

[75] Inventors: Don J. Wilen, West Hempstead; Frank Cooper, South Huntington, both of N.Y.

[73] Assignee: Computer Instruments Corporation, Hempstead, N.Y.

[21] Appl. No.: 479,291

[22] Filed: Feb. 13, 1990

Related U.S. Application Data

[62] Division of Ser. No. 278,223, Nov. 30, 1988, Pat. No. 4,949,572.

[51] Int. Cl.$^5$ .............................................. G01N 9/28
[52] U.S. Cl. ............................................................ 73/53
[58] Field of Search ................... 73/53, 439, 302, 303, 73/61 R, 61 LM, 61.1 R

[56] References Cited

U.S. PATENT DOCUMENTS

| | | | |
|---|---|---|---|
| 1,905,172 | 4/1933 | Howse | 73/303 |
| 2,604,778 | 7/1952 | Marquadt | 73/439 |
| 2,752,227 | 6/1956 | Weiland | 73/53 X |
| 3,380,463 | 4/1968 | Trethewey | 73/302 X |
| 3,460,394 | 8/1969 | Cryer | 73/439 |
| 3,476,538 | 11/1969 | Trethewey | 73/302 X |
| 4,006,636 | 2/1977 | Holmen | 73/302 |
| 4,291,575 | 9/1981 | Frissora | 73/302 |
| 4,419,893 | 12/1983 | Baillie et al. | 73/439 |
| 4,694,692 | 9/1987 | Brown et al. | 73/439 X |
| 4,711,127 | 12/1987 | Häfner | 73/302 |

FOREIGN PATENT DOCUMENTS

| | | | |
|---|---|---|---|
| 633405 | 7/1936 | Fed. Rep. of Germany | 73/302 |
| 2726223 | 1/1978 | Fed. Rep. of Germany | 73/439 |
| 3233403 | 3/1984 | Fed. Rep. of Germany | 73/302 |
| 73732 | 4/1984 | Japan | 73/302 |

*Primary Examiner*—Tom Noland
*Attorney, Agent, or Firm*—Hoffman & Baron

[57] ABSTRACT

A method is disclosed for determining physical properties of liquids, such as specific gravity or density. The method is performed through the use of a mainframe controller, a remote sensor, and two sets of dip tube assemblies, one for each of two measurement channels. The time at which a bubble is released by one of the dip tubes into a liquid and the size of the purge bubble are both controlled. By controlling the timing of bubble release, the pressure within a dip tube can b e measured after the system has been allowed to quiet down. If a pair of dip tubes is employed within the same vessel, the differential pressure can be measured when the pneumatic line pressure variations have reached steady state, that is after the gas flow into the dip tubes has been discontinued.

6 Claims, 2 Drawing Sheets

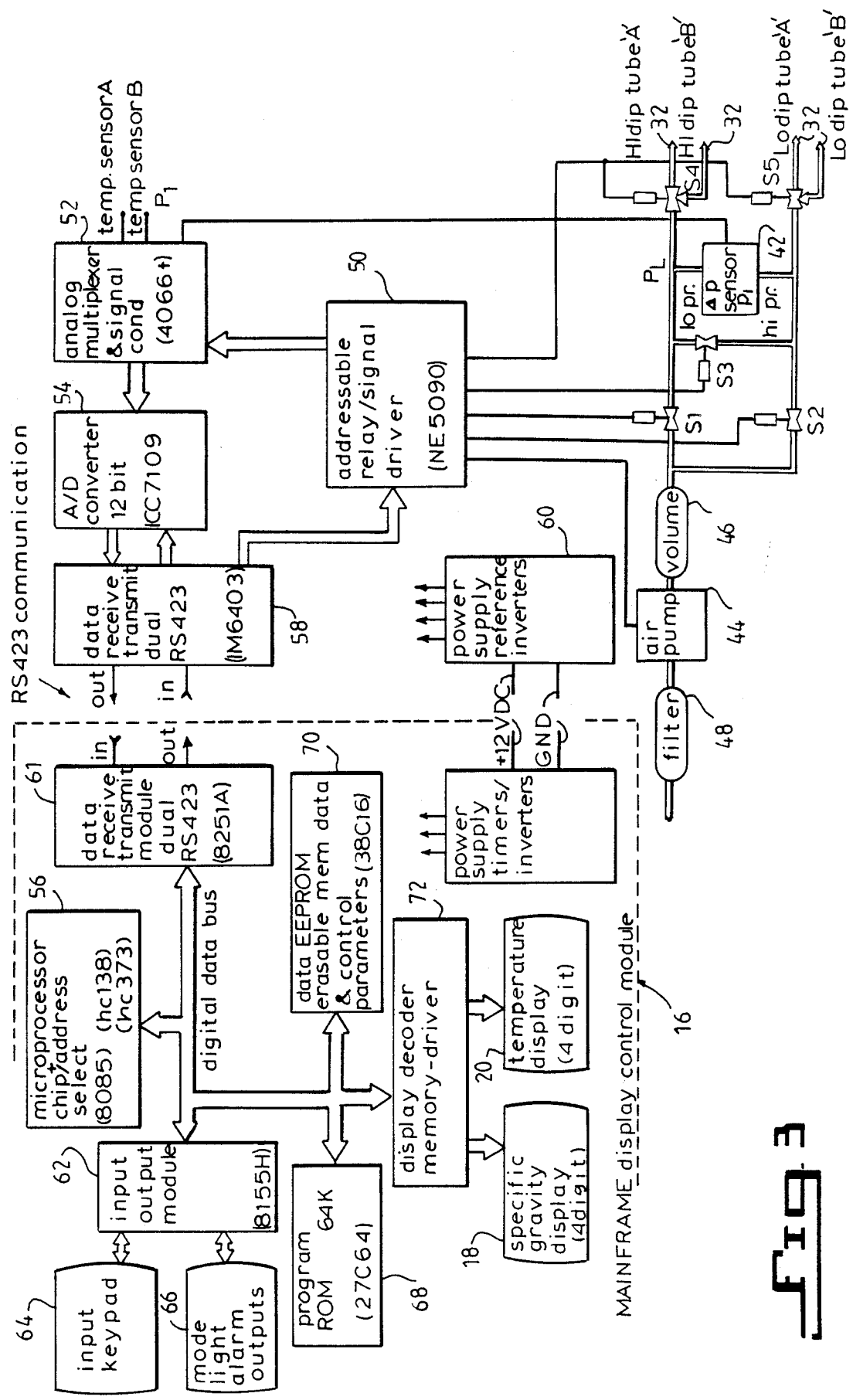

METHOD FOR DETERMINING PHYSICAL PROPERTIES OF LIQUIDS

This is a divisional of copending application Ser. No. 278,223, filed on Nov. 30, 1988, and to be U.S. Pat. No. 4,949,572.

BACKGROUND OF THE INVENTION

The field of the invention relates to systems and methods for determining physical properties of liquids, and particularly to methods which involve measuring the back pressure of a gas bubbling into a liquid.

Liquid exerts a hydrostatic head of pressure proportional to its density and depth. Bubbling a small flow of gas from a submerged dip tube causes gas back pressure which is equal to the liquid hydrostatic pressure. The gas pressure may be measured by a pressure transmitter to indicate certain characteristics or properties of the liquid. Systems employing single tubes have been frequently used to measure liquid levels. The bubble flow in such systems may be regulated to a very low level to increase the pressure in the tube until it balances the pressure at the end thereof. Pressure is then maintained at this level by the continuous release of air bubbles into the liquid.

Systems employing a pair of dip tubes have been used to measure the density of liquids and specific gravity. Such systems typically include two tubes of unequal length which are inserted within a liquid such that the end of one tube is at a different depth than the end of the other. Gas is flowed through the tubes and allowed to bubble through the liquid. The difference in pressure at the ends of the tubes is proportional to the density or specific gravity. Therefore, if a differential pressure transmitter is connected between the pair of tubes, which have a known vertical separation, the output signal can be used to calculate the liquid's density or specific gravity. U.S. Pat. Nos. 2,604,778, 3,460,394 and 4,419,893 disclose various systems which employ a pair of dip tubes through which a gas is bubbled in order to determine density or specific gravity.

Presently available and known apparatus using bubbling techniques to measure liquid level, density and/or specific gravity use a constant flow of air or other gas which is purged (bubbled) through the measured liquid from one or two vertically oriented tubes. Since pressure measurements are taken as the gas is bubbled through the liquid, the "noise" generated by the bubbles can lead to inaccurate pressure readings. Small inaccuracies are unacceptable when measuring the specific gravities of certain liquids such as the electrolyte for large lead acid storage batteries.

SUMMARY OF THE INVENTION

It is an object of the invention to provide a method for determining liquid level, specific gravity, density or other physical characteristics or properties of a liquid.

It is another object of the invention to provide an apparatus for carrying out the above method.

A still further object of the invention is to provide an apparatus including a dip tube, means for providing a pulse of purge gas to the dip tube, means for controlling when the release of a bubble occurs, and means for detecting the pressure within the dip tube during a selected period after the bubble has been released to insure the system has quieted down during the measurement period. Bubble size is also controlled by the apparatus. By controlling the purge to release a bubble of a selected size, the variations of the post purge meniscus levels at the dip tube are as small as possible. By releasing the bubble at a selected time and temporarily stopping the flow of gas into the dip tube, the pressure can be determined when the pneumatic line pressure variations have reached steady state.

If a dual dip tube system is employed, the end of each dip tube is preferably formed at an angle with respect to the respective longitudinal axes thereof. The tubes are angularly displaced with respect to each other such that bubbles released from one tube do not interfere with the proper release of bubbles from the other tube.

BRIEF DESCRIPTION OF THE DRAWINGS

FIG. 3 is a schematic illustration of the internal components of the remote sensor and display control module;

FIG. 4 is a top plan view of a dip tube assembly; and

FIG. 5 is a side elevation view thereof.

DETAILED DESCRIPTION OF THE INVENTION

Figure 1:
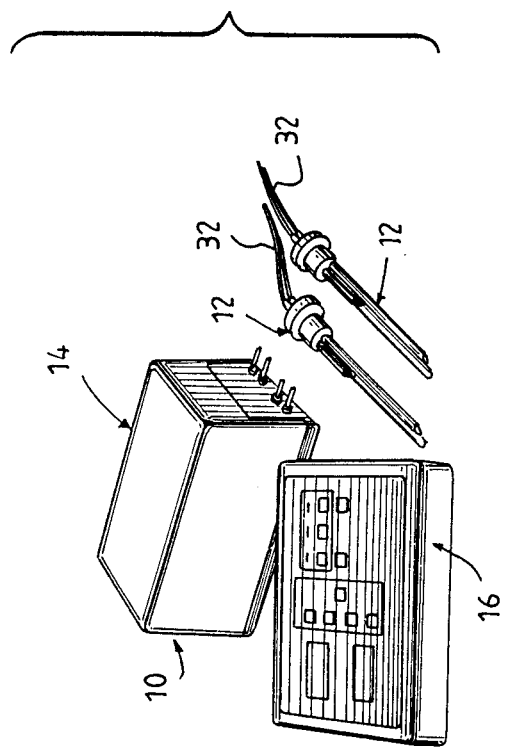
FIG. 1 is a perspective view of a system according to the invention.

A system 10 for measuring specific gravity, density, liquid level and other physical properties or characteristics is provided by the invention. The system allows the use of a particular pulsed purge and sampling technique in combination with electronic signal processing to provide fast, repeatable and accurate pressure measurements.

The system 10 includes three basic components: a pair of dip tube assemblies 12, a remote sensor 14 and a mainframe controller 16. The controller is a compact control station in an enclosure which includes a soft-touch membrane switch keypad having L.E D. displays 18, 20 for both specific gravity and temperature. The remote sensor communicates with the controller via an interface 22. It can alternatively be used with a PC based controller Multiple remote sensor units can be multiplexed with one PC controller if desired.

As shown in FIGS. 4-5 the dip tube assembly 12 includes a relatively long "low" dip tube 24 and a shorter "high" dip tube 26. Each tube is mounted to a polymeric, threaded bolt 28 having a jam unit 30 mounted thereto. A pair of resilient, polymeric tubes 32 connect each dip tube assembly to the remote sensor.

Figure 2:
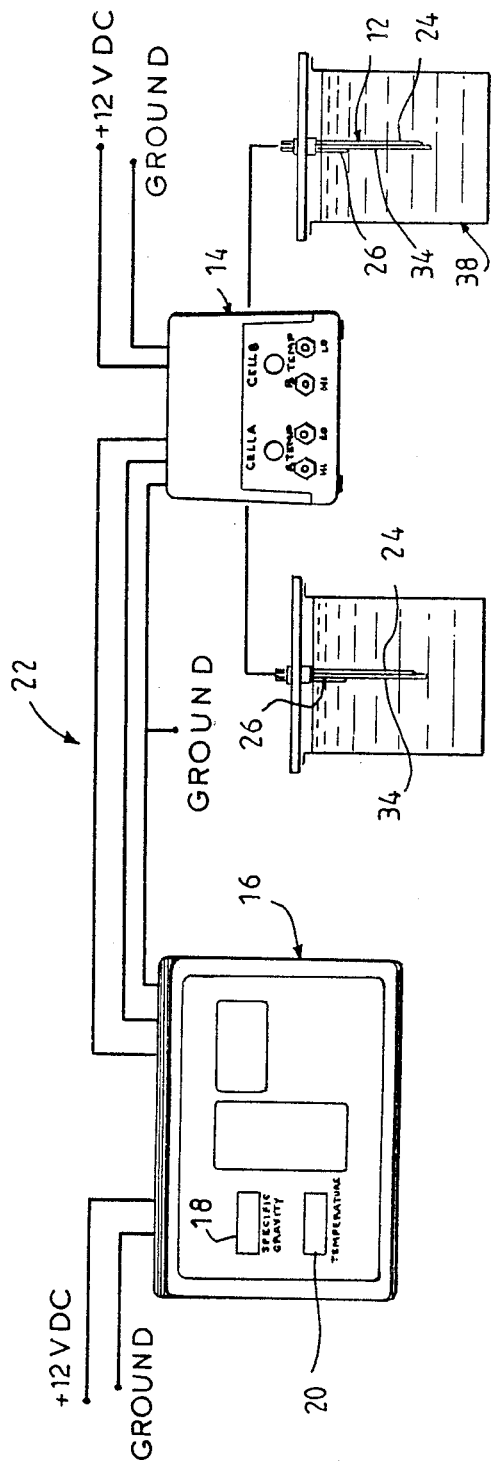
FIG. 2 is a schematic illustration of a two channel system in accordance with the invention including dip tubes, a remote sensor, and a mainframe display control module.

A temperature probe 34 is also mounted to the bolt. The probe is connected to the remote sensor by an electrical cable. A precision sensor is mounted within the temperature probe for providing an electrical output which may be converted into degrees Fahrenheit or Centigrade. A vent 36 is provided within the bolt to provide equal pressure on both sides thereof when secured to a vessel 38 (FIG. 2). An O-ring 40 is used to provide a seal between the top of the vessel and the bolt.

The end of each dip tube is designed to facilitate the breakaway of a bubble. Each end is accordingly cut at an angle (e.g. about 45°) with respect to the longitudinal axis thereof. The high and low tubes of each dip tube assembly are rotationally displaced from each other so that a bubble released from the low dip tube does not interfere with the operation of the high dip tube. The angle of rotation between the two dip tubes is preferably between 90°–180°.

The ends of each dip tube are spaced a selected vertical distance apart, preferably about six inches, when used for determining the charge state of wet-cell emergency power systems. Other distances greater than at least three quarters of an inch could be used if desired in connection with other liquids. The dip tubes should be oriented as close to vertical as possible.

Referring to FIG. 3, the remote sensor 14 includes a pair of solenoids S4 and S5 which select which of the two dip tube assemblies 12 is to be used. A different pressure sensor 42 is connected across the input/output air lines from the high and low dip tubes of the selected dip tube assembly. The pressure sensor used is a solid state, low differential pressure strain gauge sensor having a range of one to ten inches of water full scale. The sensor should have a frequency response fast enough to accurately read the measured pressure. The output of the pressure sensor is between 1–6V DC.

Solenoid S3 is used to set the differential pressure sensor equal to zero at zero pressure. In other words, $P_H = P_L$ when the solenoid is open (where $P_H$ represents the pressure within the high dip tube 26 and $P_L$ represents the pressure within the low dip tube 24). Solenoid S2 controls the purge air pulse to the low dip tube. Since the low dip tube extends more deeply into the liquid in the vessel 38 than the high dip tube, the pressure therein is relatively higher.

An air pump 44, which comprises a DC motor driven diaphragm pump, is used to provide 2–6 psi pressure to the dip tubes. (A piston pump could alternatively be employed). A cartridge 46 is provided between the pump 44 and the solenoids S1, S2 for retaining a volume of air to be used for the purge air pulse. A filter 48 prevents airborne contaminants from entering the pump.

An addressable relay/signal driver 50 (NE5090) provides the signals to operate the pump 44, relays and an analog multiplexor and signal conditioner 52. The analog multiplexor and associated twelve bit A/D converter 54 (ICC7109) select a signal from either a temperature sensor or the differential pressure sensor 42 and convert the signal to a digital (binary) form). The relay driver 50, multiplexor and A/D converter are controlled by a microprocessor 56 in the mainframe controller 16 through a data transmitter and receiver 58. The latter provides control signals to the : remote sensor 14 and data to the mainframe controller. Two RS423 data lines are used in order to be able detect any faults. A twelve volt D.C. power supply conditions the operating power as required for the electronic components of the remote sensor.

As discussed above, the mainframe controller includes a microprocessor 56 which controls the operation of the remote sensor. The microprocessor assembly further includes a chip select and address memory latch to provide control of computational facilities to perform the measurements required of the system 10. Separate chips for a one of eight chip select are provided.

A power supply 60 provides twelve volt D.C. current for the controller and also includes timers for the alarms. It further includes a power down timer that turns the unit off if it is not used for a selected period of time (e.g. one minute). A data receive/transmit module 61 (e.g. 8251A) controls the transmission of data to and from the remote sensor 14. It operates on a digital data bus with a chip select signal.

An input/output module 62 (e.g. 8155H) contains the drivers for and controls the multiplexing of the keyboard switches of the input keypad 64 and the mode lights/alarm assembly 66. The input keypad includes power-on mode controls and setpoint controls for calibration and the alarms. The mode lights/alarm assembly 66 includes light emitting diodes and piezo-electric vibrators to advise the operator of the system status.

A program ROM 68 (27C64) includes a 64K bit memory containing the operating software for operation and control, including data smoothing algorithms. A data EEPROM 70 (38C16) includes a 16K bit memory which contains field adjustable parameters such as calibration and alarm set points, purge times, and automatic mode operating times. The latter mode cycles between the two channels in an alternating manner if both dip tube assemblies are employed for a selected period of time.

A display decoder/memory driver 72 takes signals from the data bus, stores it in RAM memory, and decodes the data to drive the two four-digit displays 18, 20.

In operation, the system provides three repetitive times sequences: pulse of purge gas, bubble formation and release, and measurement. Normally during purge flow and during the time of bubble formation and release in the liquid, pressure variations occur in the purge/sense lines 24, 26 which increase measurement uncertainties. By controlling air flow and bubble formation, however, measurements can be taken during the time when the purge/sense lines have fully settled and are "quiet". This provides a more stable environment for remote pressure measurement than is achievable in a continuous air flow purge system. In addition, by controlling bubble size, the statistical variation of the post purge liquid meniscus levels is relatively small, thereby further increasing the accuracy of pressure measurements.

The operation of the system begins by setting the differential pressure sensor 42 to zero at zero pressure. The air pump 44 is actuated to generate the purge air pressure, and both purge lines 24, 26 are blown down by opening the control solenoids S1, S2. The blow down period is ordinarily about one second. A sequence of typically five to twenty cycles of operation are then run. Each cycle consists of a solenoid pulse-purge of the high dip tube 26, bubble formation and release, and measurement time. Measurement begins a selected time after bubble release when the system has quieted down. The time between bubble release (i.e. solenoid valve closure) and measurement is set by the microprocessor. The pressure sensor 42 constantly takes readings. However, data from the pressure sensor is only stored and displayed during the quiet measuring period. Best results are obtained by measuring different pressure after lower dip tube purge when gas flow into both dip tubes has temporarily been stopped. The sequential purge of high and then low dip tubes is also important to provide stable, repeatable data.

The solenoid valves S1, S2 have integral 0.035 inch orifices and may operate at speeds up to five milliseconds. Since the pump output is relatively constant during operation (2–6 psi), and the pressure required to overcome the liquid's static head relatively low (about 2–6 inches of water), the differential pressure seen by the respective orifices is substantially constant. Flow metering is governed directly by the duration or pulse width of the signal from the addressable relay/signal driver 50. As a result, a precise volume of air is accurately and electronically metered to generate one bubble. This ability to govern the bubble purge timing, size and consistency, together with the control of the post purge meniscus, enhances measurement repeatability and accuracy.

Electrical pressure and temperature readings are repeated until a new reading is within one count (A/D converter 54) of the running average of a minimum of four readings. The individual purges are continued until the pressure readings are within two counts of the running average of the last four (or more) readings.

To improve overall repeatability and to compensate for uncertainties in dip tube spacing and positioning (i.e. perpendicularity), the system includes an auto-calibration mode for allowing the operator to set a known specific gravity within the EEPROM data memory so that all readings are relative to this "calibrated" value.

The system 10 may be used to determine the charge state of wet-cell emergency power systems, where sampling two cells is generally considered adequate for a fifty battery reserve. The system can be used to measure specific gravity, temperature or liquid level in both laboratory and industrial environments. The two channels are completely independent and can simultaneously be used with unrelated liquids. A programmable set-point alarm is provided for each channel for both specific gravity and temperature. These "out of range" alarms, (which include the mode lights/alarm output assembly 66) when used in conjunction with a variable interval automatic mode, provide continuous monitoring suitable for automated or unmanned facilities.

The system may also be used in mixing or batching operations using liquids of known densities, to determine solvent purity, flux density, or water content in acids, bases or alcohol. It can be used in connection with dissolved or suspended solids, such as supersaturated salt baths (density indication), TEFLON in water (percent solids), coal in water (percent solids), coal in water (percent solids), and precious metals in plating solutions.

Rather than measuring pressure a fixed time after solenoid valve closure, the system could be operated by detecting a "blip" in the pressure readings caused by release of a bubble. Once the pressure readings have settled down after this "blip", the data transmitted by the pressure sensor would be reliable.

What is claimed is:

1. A method for determining the physical properties or characteristics of a liquid or suspension, comprising:
   providing a dip tube having an open end;
   providing a vessel containing a liquid;
   inserting said open end of said dip tube into said liquid;
   flowing a selected volume of gas into said dip tube such that a bubble is released from said dip tube into said liquid;
   discontinuing said flow of gas into said dip tube upon release of said bubble; and
   detecting the pressure within said dip tube while said flow of gas into said dip tube has been discontinued.

2. A method as defined in claim 1 wherein said step of flowing said selected volume of gas into said dip tube causes the release of one bubble.

3. A method as defined in claim 1 including the steps of:
   providing a second dip tube having an open end;
   inserting said second dip tube into said liquid such that said open end of said second dip tube is at a different depth than said open end of said other dip tube;
   flowing a selected volume of gas into said second dip tube while said flow of gas into said other dip tube has been discontinued, thereby releasing a bubble into said liquid;
   discontinuing said flow of gas into said second dip tube; and
   detecting the pressure within said second dip tube while said flow of gas into each of said dip tubes has been discontinued.

4. A method as defined in claim 3 wherein said step of flowing a selected volume of gas into said second dip tube causes the release of one bubble.

5. A method as defined in claim 3 wherein said open end of said second dip tube is positioned deeper, within said liquid than said open end of said other dip tube, including the steps of flowing said selected volume of gas into said second dip tube after flowing said selected volume of gas into said other dip tube, and detecting the pressure within each of said dip tubes while said flow of gas into each of said dip tubes has been discontinued.

6. A method as defined in claim 3 wherein said steps of detecting the pressure within each of said dip tubes includes detecting the differential pressure between said dip tubes.

* * * * *